United States Patent [19]

Faccioli et al.

[11] Patent Number: 5,433,720

[45] Date of Patent: * Jul. 18, 1995

[54] CENTERING MEANS FOR HOLES OF INTRAMEDULLARY NAILS

[75] Inventors: Giovanni Faccioli, Monzambano; Stefano Rossi, Verona, both of Italy

[73] Assignee: Orthofix S.r.l., Bussolengo, Italy

[*] Notice: The portion of the term of this patent subsequent to Mar. 1, 2011 has been disclaimed.

[21] Appl. No.: 121,762

[22] Filed: Sep. 15, 1993

Related U.S. Application Data

[63] Continuation-in-part of Ser. No. 618, Jan. 5, 1993, Pat. No. 5,281,224.

[30] Foreign Application Priority Data

Sep. 22, 1992 [IT] Italy .................. VR92A081

[51] Int. Cl.⁶ .................... A61F 5/00; A61F 2/32
[52] U.S. Cl. ............................ 606/87; 606/98
[58] Field of Search ..................... 606/62–68, 606/96, 97, 98, 86, 87, 88

[56] References Cited

U.S. PATENT DOCUMENTS

| | | | |
|---|---|---|---|
| 4,526,177 | 7/1985 | Rudy et al. | |
| 4,653,487 | 3/1987 | Maale | 606/62 |
| 4,667,664 | 5/1987 | Taylor et al. | |
| 4,791,919 | 12/1988 | Elloy | 606/62 |
| 4,952,213 | 8/1990 | Bowman | 606/62 |
| 4,976,713 | 12/1990 | Landanger | 606/62 |
| 5,013,317 | 5/1991 | Cole | 606/97 |

FOREIGN PATENT DOCUMENTS

2842203 4/1980 Germany .

Primary Examiner—Michael A. Brown

[57] ABSTRACT

A jig is detachably secured to the proximal end of an installed intramedullary nail having a transverse bolt hole near the distal end of the nail. The jig comprises an offsetting arm which so mounts the proximal part of hinged elongate template structure as to render the distal part thereof angularly movable in a geometric plane substantially parallel to the nail. One or more spaced guide bores near the distal end of the movable distal part is on an axis perpendicular to the geometric plane. When the jig is chucked to the nail, the axes of the one or more guide bores of the template are parallel to the axes of one or more bolt holes of the nail; and corresponding guide-bore axis and bolt-hole axes are at identical distance from the offsetting arm. The distal end of the template is adapted to removably mount a metal-detector establishing a magnetic field about a directional axis, such that the metal-detector can be scanned on one side and then the other side of a central position in which the directional axis of the detector locally intersects the axis of the nail. Associated electronic circuitry takes note of template positions at which equal detector signals occur on opposite sides of the central position has been achieved, and a microprocessor component of the circuitry automatically calculates and displays a value representative of the calculated "center" position.

21 Claims, 4 Drawing Sheets

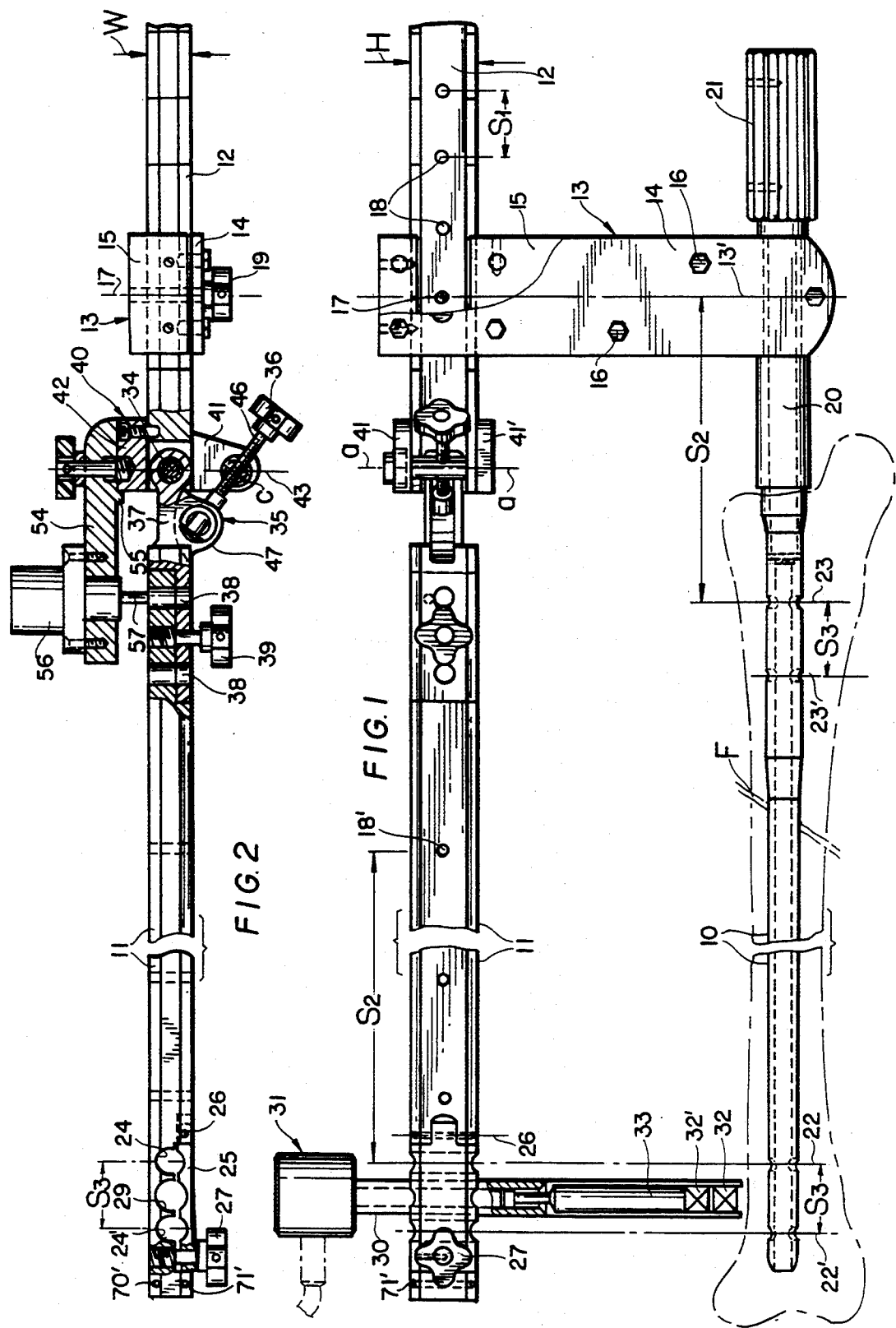

CENTERING MEANS FOR HOLES OF INTRAMEDULLARY NAILS

RELATED CASE

This application is a continuation-in-part of patent application Ser. No. 08/000618, filed Jan. 5, 1993 (now U.S. Pat. No. 5,281,224, issued Jan. 25, 1994.

BACKGROUND OF THE INVENTION

This invention relates to centering means for holes of intramedullary nails, of the type used in bone surgery.

For the surgical repair and stabilization of fractures of long bones, such as the femur, tibia, humerus and fibula, it has long been known to insert an intramedullary nail of appropriate length into the medullar cavity, and to anchor bone fragments to the nail. Anchorage is achieved by means of bolts or pins which are screwed into the walls of the bone on opposite sides of the medullary cavity, and these bolts or pins pass through transverse holes located in the vicinity of the proximal and distal ends of the intramedullary nail. The anchoring bolts are held in position until confronting edges of the broken bone have completely grown back, and are then extracted to allow the intramedullary nail to be removed. The procedure for inserting the holes requires (a) accurate location of the transverse holes in the intramedullary nail, (b) drilling through the cortical and spongy tissue of the bone to provide passages for the bolts, and (c) inserting bolts in such a way as to secure the nail in a suitable position with respect to the bone fragments.

The most critical part of this procedure is to determine, from outside, the location and center of so-called blind holes in the nail; this must be done with the maximum possible accuracy in order to avoid any misalignment of drilled holes and repeated drilling of the bone.

The known method of centering provides for the use of a drilling mask or frame consisting of a longitudinal template which can be attached to the intramedullary nail at its proximal end and which is provided with holes to house bushes for drilling the bone at positions aligned with the holes in the nail.

The centering of holes toward the proximal end of the intramedullary nail, close to the area of attachment to the frame, is a relatively simple operation which does not give rise to any special problems. On the other hand, the centering of blind holes near the distal end of the intramedullary nail is very much more difficult because of the elasticity of the template, and play in the vicinity of coupling between the frame and the intramedullary nail.

A great many centering devices have been proposed, using orientable drilling bushes or a more rigid drilling template with less play in the frame/nail coupling. However, none of these proposed arrangements have been sufficiently rigid; as a result, these proposed arrangements do not ensure the accuracy which is needed for repeatable precision drilling at the distal end of the nail.

It should also be noted that all the known centering devices mentioned above require an X-ray source, which is used by the surgeon to check the hole location with respect to the outer surface of the patient's limb.

The known techniques are hazardous because they require the patient and healthcare personnel surrounding him to suffer repeated and prolonged exposure to X-rays, which are well known to be harmful beyond certain limits, but which cannot be switched off without compromising the final result of an operation. Also, X-rays cannot be used to accurately establish the axial orientation of a hole with respect to the external surface of the limb because the X-ray image is projected onto a plane and cannot be used for a clear determination of any errors in the inclination of the hole.

U.S. Pat. No. 4,667,664 discloses a centering device for the blind holes of an intramedullary nail, wherein a bar supports an X-ray aiming device at one end and the intramedullary nail at the other end; the device is provided with a stabilizing member comprising an arm which connects a median portion of the bar to an intermediate point, between the proximal and distal ends of the nail. But even this device is not sufficiently stable with respect to the distal end of the nail, and therefore the device does not offer maximum assurance of accuracy and stability in the drilling of bone at a distal location. Also, this device again makes use of X-rays, and is therefore unreliable and unsafe.

In our copending Italian application VR92A000081, filed Sep. 22, 1992, we disclose an improved hole-centering device and technique for locating blind distal-end holes in an installed intramedullary nail, whereby use of X-rays is avoided. The disclosure of said copending application is hereby incorporated by reference. However, it is helpful here to summarize that, in said copending application, a jig is detachably secured to the proximal end of an installed intramedullary nail having a transverse bolt hole near the distal end of the nail. The jig comprises an offsetting arm which so mounts an elongate template that its distal end can be flexibly deflected in a geometric plane substantially parallel to the nail. A guide bore near the distal end of the template is on an axis perpendicular to the geometric plane. When the jig is chucked to the nail, the axis of the guide bore of the template is parallel to the axis of the bolt hole of the nail, and both the guide-bore axis and the bolt-hole axis are at identical distances from the offsetting arm. The distal end of the template is adapted to removably mount a metal-detector or probe establishing a magnetic field about a directional axis, such that the metal-detector can be selectively moved or positioned on one and then on the other side of a central location in which the template is locally effectively parallel to the nail. Template positions noted for equal detector signals on opposite sides of the central location enable determination of the central location and therefore the point at which the template guide bore is in axial alignment with the bolt hole of the nail. As disclosed in said copending application, a fixed reference must be first established to the distal end of the involved bone, for support of the otherwise cantilevered distal end of the flexibly deflectable template, with provision for controlled measurable deflection and subsequent clamping of the template to the fixed reference, once the center point has been identified as the half-way location between the two points at which the two equal signals were obtained.

BRIEF STATEMENT OF THE INVENTION

It is an object of the present invention to provide an improved apparatus and technique for location of blind holes in an installed intramedullary nail, without requiring use of X-rays.

A specific object is to achieve the above object without requiring flexible deflection of a template or any other part of the apparatus.

Another specific object is to meet the above objects with a single template construction which is universally applicable to the location of blind intramedullary-nail holes, for a range of sizes of intramedullary nails and for establishing drill-hole alignments of both distal-end and proximal-end holes throughout such a range.

A further specific object is to meet the above objects with apparatus which does not require a fixed distal-end reference to an afflicted bone, for the ascertainment of a correctly centered distal drill-hole alignment of a blind distal bolt hole of an intramedullary nail.

It is also a specific object to provide such an improved apparatus with an adjustably displaceable template, and incorporating the feature of digitally displaying a calculated nail center so that adjustment can be made to the point of matching the instantaneous template position to the displayed calculated value.

The invention achieves these objects, for the case of an intramedullary nail having proximal and distal ends, with plural transverse holes close to these ends, by providing a jig or frame structure for supporting drill guides from outside the involved limb. The frame comprises a two-part elongate template wherein a distal part has pivotable articulated connection to a proximal part. The distal part has transverse guide bores for drilling tools, and these guide bores are spaced to accord with at least the spacing of a pair of the transverse holes of the intramedullary nail. The frame further comprises a transverse or offsetting arm for removable attachment to the proximal end of the nail and for removable attachment to the proximal part of the template, such that the proximal part of the template is parallel to the nail, with the distal part of the template displaceable in a geometric plane which is normal to the direction of arm offset, with distal-end template bores at approximately equal offset from and for potential alignment with holes of the nail. Adjustment of articulated displacement of the template parts about the pivot axis is precisely sensed and is presented as a numerical display of instantaneous positional value. A metal-detecting instrument carried near the distal end of the distal part of the template is capable of detecting and calculating the "center" position wherein guide-hole axes at the distal end of the template are sufficiently aligned for local blind intersection with the axis of the nail and therefore for alignment with the axes of transverse holes at the distal end of the nail; output of this instrument is a calculated numerical display of the correctly "centered" position, and the operator moves the distal part of the template until the displayed instantaneous-position value matches the display of the calculated "center" position.

DETAILED DESCRIPTION OF A PREFERRED EMBODIMENT

The invention will be described in detail, in conjunction with the accompanying drawings, in which:

FIG. 1 is a view in side elevation of a jig of the invention in operative position with respect to an intramedullary nail, shown in application to a bone between distal and proximal fragments of the bone;

FIG. 2 is a plan view of jig components of FIG. 1;

Figure 3:
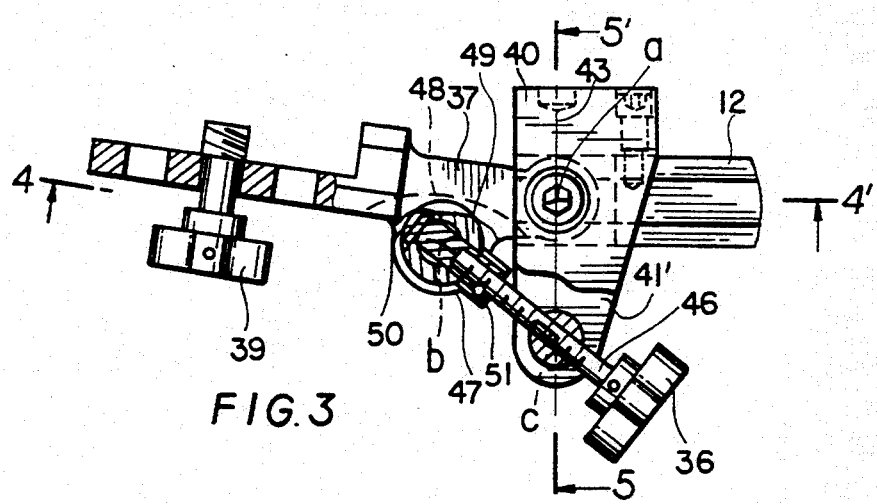
FIG. 3 is an enlarged fragmentary plan view, partially in section, for articulated parts of the jig of FIGS. 1 and 2.

The hole-centering means or jig of the invention is seen in FIG. 1 in application to a bone (phantom outline) having a fracture F between longitudinal ends of the bone, and an intramedullary nail 10 will be understood to be positioned in the medullar cavity for repair of the fracture F; nail 10 is of metal, preferably stainless steel. The jig comprises template structure in the form of an elongate distally extending first part 11 and an elongate proximally extending second part 12 having generally central articulating connection via a pivot axis a which is in the vertical plane of symmetry of the section of each of the parts 11, 12.

Use of the terms "vertical" and "horizontal" herein will be understood to be solely to enable a more simple description of parts and their relationship, inasmuch as there is no requirement of the invention that parts should be necessarily gravitationally vertical or horizontal. Thus, for simpler presentation, FIG. 1 is describable as a side-elevation view of parts which are in a "vertical" plane, namely the plane of the drawing, and the "horizontal" direction will be understood to apply to the right-left direction of parts of FIG. 1, while the horizontal plane is taken as a plane normal to the plane of the paper and including, for example, the central axis of the elongate parts 11, 12.

The preferably identical cross-section of each of the parts 11, 12 may be octagonal, the product of aluminum extrusion, wherein the vertical height H exceeds the lateral width W by a factor of 3:2, thus providing a greater cross-sectional moment of inertia in the vertical plane for resistance against droop of cantilevered structure, as well as a substantial but lesser moment of inertia in the horizontal plane, for resistance against lateral bending along the length of either of parts 11, 12.

A rigid offsetting arm 13 comprises front and back plate parts 14, 15 which are releasably clamped to each other, as by bolts 16, and to the distally extending part 12, the particular longitudinal location of clamping the upper end of arm 13 to part 12 being a matter of choice of registration of a transverse-bore alignment 17 with a selected one of plural such bore alignments 18 at preferably equal spacings $S_1$ along the length of the proximally extending part 12. A manually operated knob 19 is the head of a shank or pin for assuring that the fixed connection of arm 13 is at a precisely selected location along part 12.

At its lower end, arm 13 is secured to chuck mechanism, associated with a mandrel 20 and with manual means 21 for operating the chuck mechanism for releasable engagement to and axial alignment with the proximal end of the intramedullary nail 10. This chucked engagement will be understood to involve coacting keying features of nail 10 and of the chuck mechanism, whereby the transverse alignments of distal-end bolt holes 22, 22' and of proximal-end bolt holes 23, 23' in nail 10 are all in the vertical plane of symmetry of the elongate parts 11, 12 of the template structure. Thus, as long as nail 10, arm 13 and the proximally extending part 12 are locked in substantially the same vertical plane, articulated pivoting of the distally extending part 11 is in a horizontal plane that is parallel to the axis of nail 10 or, at least to the axis of nail 10 at its region of chucked support by mandrel 20 at the lower end of arm 13. It will also be observed at this juncture that a fixed and precisely defined longitudinal distance $S_2$ is defined between the axis of the nail bolt hole 23 and the right-angle related axis 13' of selective location (via axis 17) of arm-13 clamping to the proximally extending part 12. And it will be further observed that a fixed longitudinal spacing $S_3$ exists between the pair of distal-end bolt-hole centers of nail 10, between the pair of proximal-end bolt-hole centers of nail 10, and between centers for guide-sleeve clamping bores 24, 24' at the distal end of the distally extending part 11 of the template structure.[1] A clamp arm 25 having hinge connection at 26 to part 11 is actuable by manually operated means 27 into positively retained and oriented location of such sleeves (not shown) for later drill guidance within the respective sleeves and on the vertical alignments of axes 24, 24'.

[1] This fixed spacing $S_3$ accords with the standard spacing between bone-screw clamp features at the respective longitudinal ends of an external fixator, which will ultimately be relied upon to fixedly retain the broken halves of the fractured bone.

The distal-end clamp bores 24, 24' will be understood to be at the same longitudinal spacing from the perpendicular axis 13' of arm 13 as are the corresponding distal-end bolt-hole alignments at 22–22' of nail 10. And at the midpoint between bores 24, 24' the distal-end clamp includes a third bore 29 that is sized for adjustably mounting the elongate stem 30 of a metal-detector device or probe 31, with the central axis of stem 30 parallel to axes of bores 24, 24'. The device 31 is preferably of known magnetic construction wherein first and second like windings 32, 32' are developed in spaced relation on a ferrite core 33, near the lower end thereof. The upper half of stem 30 may be of aluminum tubing, containing excitation leads between coils 32, 32' and an upper housing of electronic excitation and detection components. The lower half of stem 30 is devoted to core 33 and its windings, which may be potted in epoxy to the cylindrical dimension of the upper half. In the absence of a metal presence near the lower end of stem 30, the excitation of coils 32, 32' develops a magnetic field that is symmetrical about and beyond the axial center of core 33, and the presence of a metal within this field will produce a detector output signal which is of greatest magnitude when the metal is closest to the lower end of core 33, said magnitude reducing for departure of the core alignment either side of the closest alignment; this signal and its use in the invention will be further discussed below in connection with FIG. 6.

Figure 4:
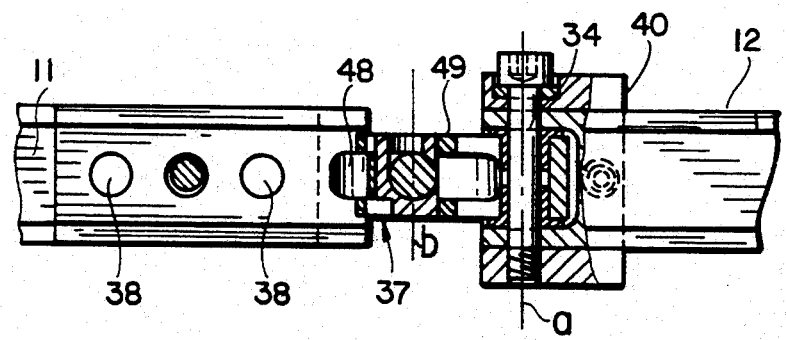
FIG. 4 is a similarly enlarged fragmentary side-elevation view, partially in section, for the articulated parts of FIG. 3, wherein the viewing aspect 4–4' follows a course via pivot axes a, b of FIG. 3.
Figure 5:
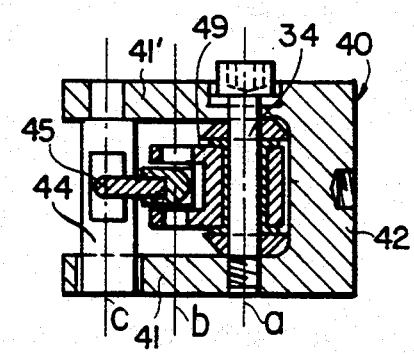
FIG. 5 is a view from the aspect 5–5' of FIG. 3, taken on a course via pivot axes a, b, c of FIG. 3.

An overall description of the device of FIGS. 1 and 2 is completed by discussion of the means of articulation about axis a, and additional reference is made to FIGS. 3, 4 and 5, which deal with detail of the pivotal connection of parts 11, 12, via a hinge assembly 35, which permits manual adjustment (at 36) of the angular relation of parts 11, 12 about axis a, and which also permits removable connection of part 11, so as to enable adaptation to a selected one of a range of template lengths for the distally extending part 11. As shown, the assembly 35 comprises a short rugged arm 37 which has pivotal-bearing connection via a pintel 34 to the adjacent end of the proximally extending part 12 of the overall template structure. At its other end, arm 37 has been milled for lapped registration with the adjacent, similarly milled end of part 11. Spaced dowel pins 38 carried by part 11 register with locating bores in the lapped region of arm 37 and part 11, and the accurately assembled relation of arm 37 to its selected part 11 is secured by a clamp screw between the dowel pins, manually actuable at 39.

A generally U-shaped bracket 40 comprises spaced upper and lower arms 41, 41' extending from a connecting base 42 which is bolted to a lateral side of part 12, with arms 41, 41' in seated engagement with upper and lower surfaces of part 12. Arms 41, 41' establish a transverse offset for a second pivot axis c which is parallel to the articulation axis a and which is also preferably on an alignment 43 of axes a and c perpendicular to the vertical plane of symmetry of part 12. A boss or hub 44 is journaled in and between arms 41, 41' for angular displaceability about axis c, and boss 44 has a centrally located diametrically extending bore 45 that is threaded for the lead-screw length of an adjustment rod 46 which is manually driven by means 36.

A laterally offset bulging formation 47 is centrally milled to a recessed concave arcuate contour 48, to thereby define vertically spaced upper and lower ears which are bored on a third axis b for journaled support of a hub or boss 49, which receives actuating displacement adjustments from the lead-screw adjustments at 36, to determine angular setting of arm 12 about the articulation axis a. To this end, hub 49 is shown with a centrally located diametrically extending bore in which a headed pin or stud 50 is rotatable but axially captive by reason of a collar 51 that is transversely pinned to the projecting end of the stud; this projecting end of the stud is bored for inserted accommodation of the adjacent end of the lead-screw stem 46, and the pin which secures collar 51 to stud 50 also secures stud 50 to the end of the lead-screw stem 46. The head of stud 50 and collar 51 ride opposed bearing flats of hub 49, so that they can rotate with the lead screw for adjustments made at 36, but at the same time their bearing against the opposed flats of the hub enables smooth, finely adjusted torquing of arm 37 about the articulation axis a.

FIG. 2 additionally shows an extension arm 54 having a shoulder or rib 55 for accurately nested reference to a corner between orthogonal flat vertical surfaces of the base 42 of bracket 40. The extension arm 54 provides a mounting base for a displacement transducer 56 having an internally guided rod 57 that is spring-loaded for continuous contact with the adjacent side wall of part 11; rod 57 thus responds to changes in distance of the transducer with respect to part 11, whatever the adjusted angle of articulation of parts 11, 12 about axis a. As shown, extension arm 54 and the transducer mounted thereto constitute an independent assembly which relies on a captive threaded member having an actuating knob 58 for securing the assembly to the adjacent end of part 12, via the base 42 of bracket 40. The transducer 56 may be a commercial device, available from various sources, and it is indicated that the potentiometer-based displacement products of RS Components SpA (Italy) are entirely satisfactory, with present preference for a particular such product wherein a potentiometer range of 5K ohms is linear within ±2 percent, for a travel distance of rod 47 displacement over a range of 10 mm.

Figure 7:
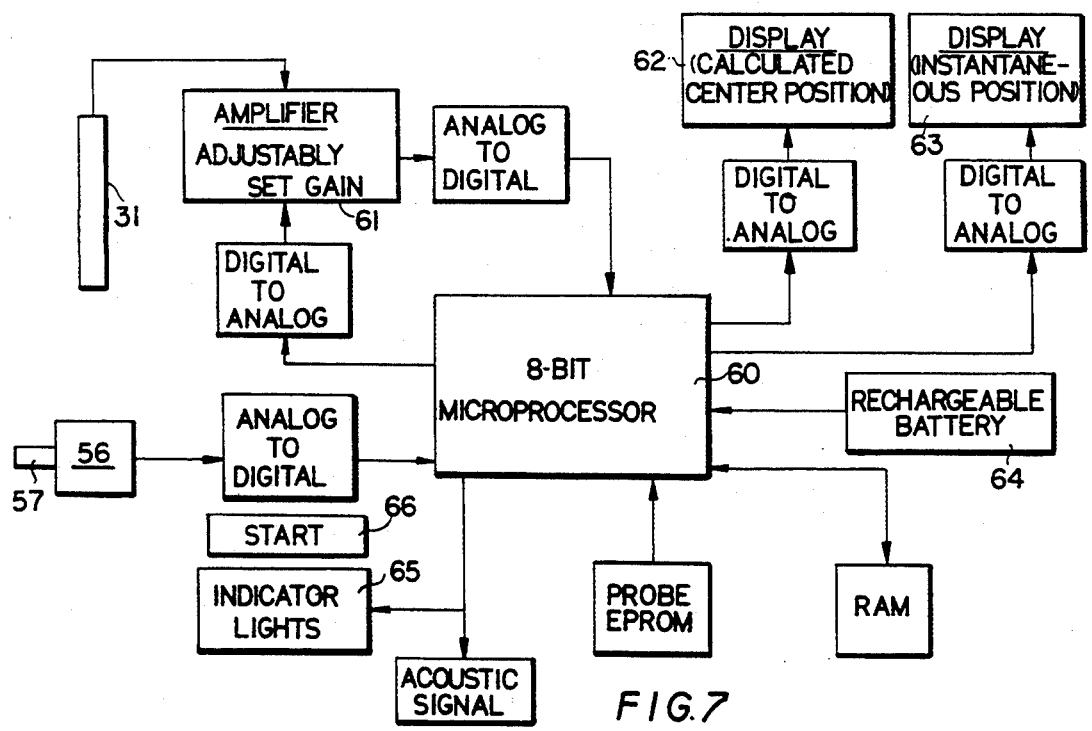
FIG. 7 is a simplified electrical block diagram of circuitry involved in operation of the invention.

Referring now to FIG. 7, it will be seen that a single microprocessor 60, powered by a rechargeable battery, can concurrently serve the coordinated outputs of the metal-detector probe 31 and the potentiometer 56 which tracks instantaneous angular position. Analog-to-digital conversion of the output of the potentiometer 56 over the indicated 10-mm range of rod 57 displacement is divided by an 8-bit microprocessor 60 into 255 discretely countable steps. This is the capacity of the microprocessor within the linear operating range of the potentiometer. But the needed angular displacement of arm 11 about axis a is a lesser figure, in that for an angular sweep of metal detector 31 across potential alignment with nail 10, a 20-mm displacement of the probe stem is typical and likely to be involved, with some ambiguity as to the center of such displacement; for an assumed but typical 5:1 proportion of the radial offset of stem 33 from axis a, as compared with the radial offset of the point of engagement of rod 57 with part 11, only a 4-mm displacement of rod 57 need be used, and this translates into use of approximately 100 of the available 255 digital steps within the linear capacity of the potentiometer and the microprocessor.

Figure 6:
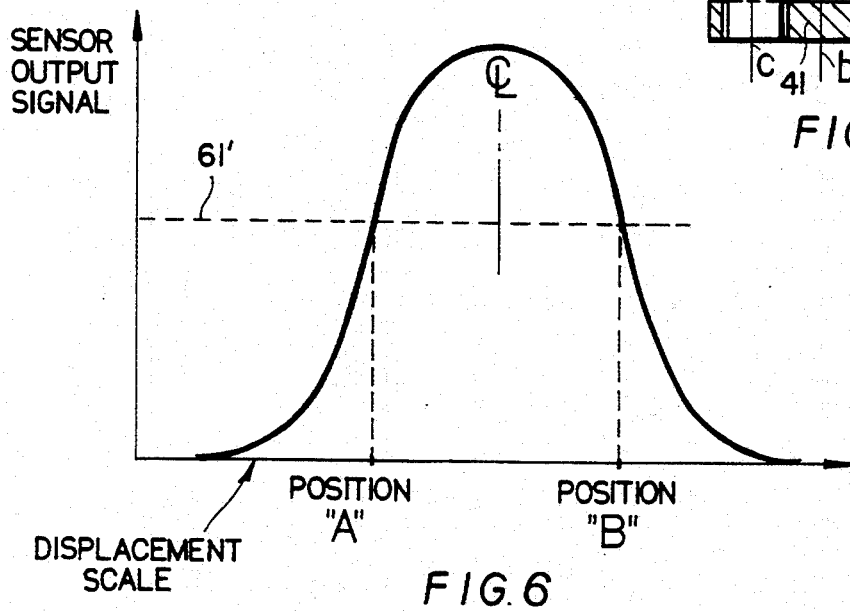
FIG. 6 is a diagram to illustrate electrical signal output of a metal-detector component of the jig of FIG. 1.

The signal output of the metal detector 31 follows the generally Gaussian curve of FIG. 6, in the course of displacing the axis of detector stem 33 from one to the other side of local intersecting alignment with the axis of nail 10. This signal is converted from analog to digital, for another input to the microprocessor. And an output from the microprocessor, converted to analog, is used for setting the threshold of an amplifier 61, whereby only metal-detector signals above threshold are utilized in the computation of the nail-center alignment position; in FIG. 6, the level 61' identifies this threshold, with which like opposed offset positions A and B apply, on opposite sides of probe-33 alignment with the axis of nail 10.

Amplifier 61 is schematically shown with provision for self-adjustment of gain, pursuant to a determination by the microprocessor as to the maximum detected amplitude of the probe (31) signal in the course of an initial sweep of the mounted probe from one to the other side of the nail 10, it being noted that the magnitude of maximum probe (31) signal is a function of probe-tip proximity to nail 10, and bones of different size will necessarily mean a different proximity, from one to the next patient application. The threshold 61' is automatically determined by the microprocessor to accord with the region of steepest slope of the signal (FIG. 1), namely, generally in the range of 30 to 70 percent of detected maximum signal; suitably, the threshold 61' may be at substantially 55 percent of the detected maximum.

Separate displays, suitably numerical displays at 62, 63, are provided by the circuit of FIG. 7, for operator use in assuring that the angle-adjustment knob 36 has correctly moved part 11 into the correct microprocessor-computed value of the true center of magnetic-probe response to the presence of nail 10. As indicated by legend, display at 62 is numerical, representing the calculated "center" position, and display at 63 is a numerical presentation of instantaneous angular position (i.e. rod-57 displaced position) within the full 255-step range of potentiometer 56 linearity.

Operating procedure will be described, assuming that the jig has been assembled to the installed intramedullary nail, as described, (i) with the potentiometer/transducer 56 in place; (ii) with the metal-detector stem 30 so vertically clamped at 27 as to position the lower end thereof in close but non-contacting proximity with the patient's afflicted limb; (iii) with knob 36 adjusted to shift the angularity of part 11 enough for a first approximation of alignment of the axis of stem 30 for local intersection with the nail axis; and (iv) with functioning electronic circuitry connected to the power source (e.g., battery 64) for a sufficient warm-up period, indicated by a clamp at 65. Having thus prepared, press the START button 65 to initiate an illustrative succession of steps as follows:

(a) Self-Adjustment Of Amplifier (61) Gain for optimal response to the output signal of the metal-detector or probe 31. On a first angular sweep of probe 31 over nail 10, the microprocessor will be understood to have been programmed to evaluate the detected maximum of the probe (31) signal which, it will be recalled, is a function of probe-stem proximity to the nail. Based on its evaluation of this detected maximum, the microprocessor adjusts the gain setting of amplifier 61 and also sets the threshold 61' for identifying a signal level at which distance measurements from potentiometer 56 are to be utilized. Once these settings have been automatically effected, an acoustic signal and another lamp at 65 will announce completion of this self-adjusting task, and that the device is therefore ready for the next step.

(b) Data Acquisition. The operator slowly and repetitively scans the bone from side-to-side by adjusting (at 36) the angle of the articulating jig part 11, taking care that the probe stem 30 makes no physical contact with anything in the course of scanning. The display at 63 will always numerically display the instantaneous potentiometer (56) reading of scan position, which may initially, i.e., before scanning, read something such as "120" between limits 0 to 255 of the indicatable range but not necessarily the center of the range. Scanning is continued until an acoustic signal and another lamp at 65 indicate that threshold 61' has been crossed at least once but preferably several times on both sides (Positions "A" and "B") of the central peak of probe response, and that the device has acquired sufficient data and is ready for the third step.

(c) Calculation of the Center. By means of software associated with the microprocessor, the positional data for opposite crossings of threshold 61 are stored, and the center of nail 10 is calculated. Once calculated, this will appear as a numeric value (e.g. "146") at display 62. An acoustic signal and a green light at 65 will announce that the device is ready for the fourth step, it being noted that throughout the scanning (i.e., at least in the range defined by and between threshhold 61' intercepts with the curve of the probe (31) signal), the instantaneous-position display at 63 remains continuously operative.

(d) Probe (31) Positioning at the Center. The operator notes the calculated display value (e.g. "146") at 62, as well as the instantaneous-position display value at 63, and to the extent that there is a difference, knob 36 is adjusted to bring the instantaneous-position number displayed at 63, into equality (e.g. "146") with the calculated-value display at 62.

At this point, guide axes 24, 24' are correctly aligned with bolt-hole axes 22, 22' of the intramedullary nail, and it is recommended that a K-wire be inserted into the distal metaphysis of the bone, without application of force, to stabilize the position of the jig. The clamp 25 may then be relaxed, for removal of probe 31 and insertion of two distal screw guides, and their drill guides, at bores 24, 24'. Drilling via the drill guides should be without application of force, prior to screw insertion.

Figure 9:
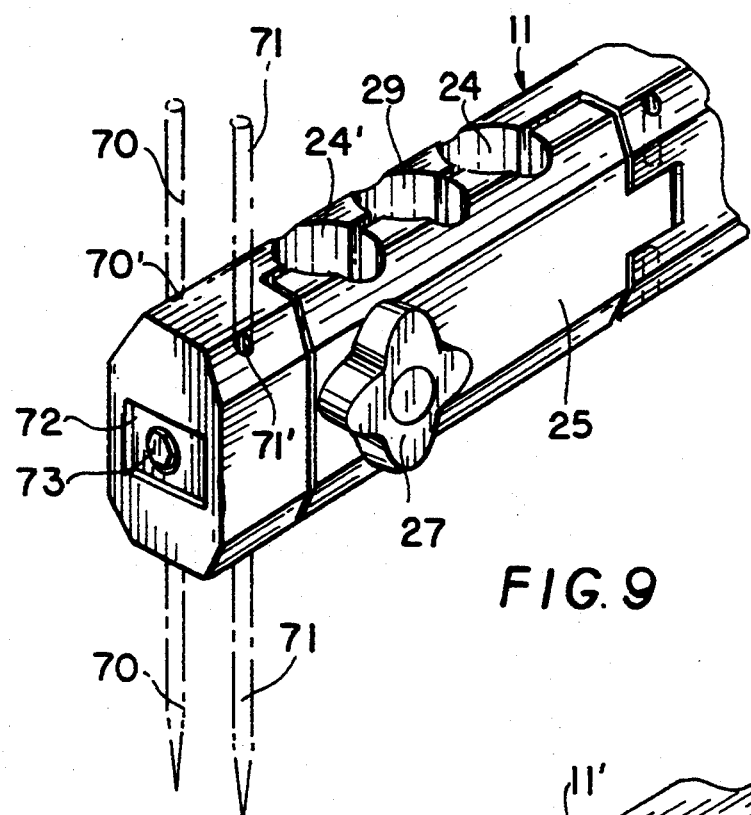
FIG. 9 is an enlarged fragmentary view in perspective of the distal end of jig components of FIGS. 1 and 2.

In illustration of the K-Wire use mentioned above, the fragmentary view of FIG. 9 shows (in phantom) two laterally spaced K-wires 70, 71 at the distal end of the distal template part 11, the same deriving vertically adjustable guidance in laterally spaced vertical bores 70', 71' (see FIGS. 1 and 2) in said distal end. A distally exposed clamp plate 72 and bolt 73 serve to secure said distal end to the metaphysis of the bone.

Figure 10:
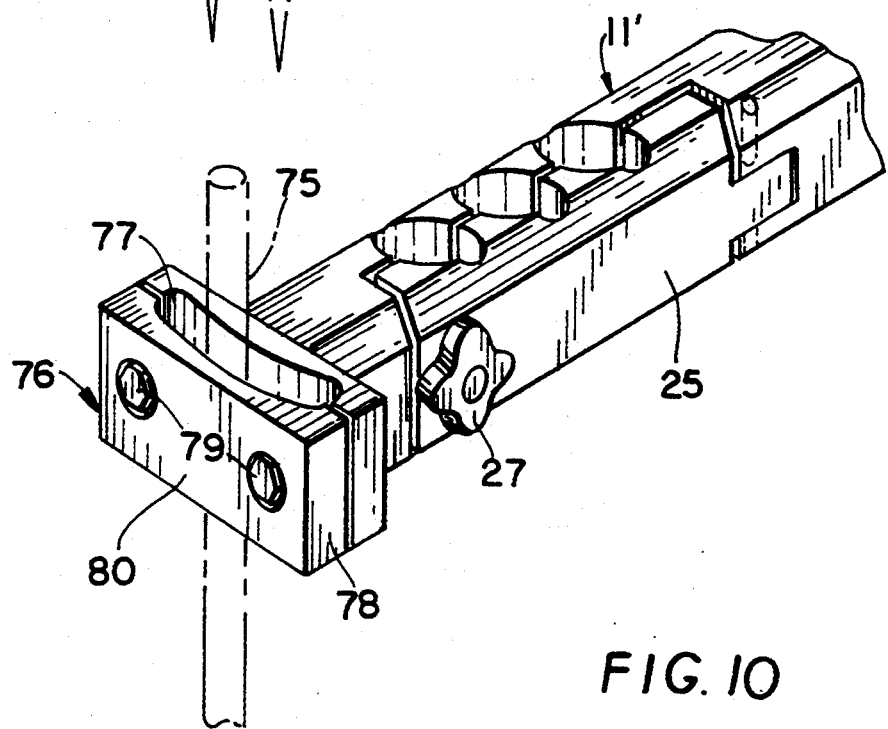
FIG. 10 is a view similar to FIG. 9 for a modification.

As an alternative (FIG. 10), for greater rigidity of the distal template connection to the metaphysis of the bone, a solid Steinmann pin 75 will be understood to have been vertically inserted in the metaphysis of the bone, at a location distally beyond the intramedullary nail, and, prior to any electromagnetic probing for location of the intramedullary nail center. In the case of FIG. 10, the distal end 76 of template part 11' is formed with a cylindrically arcuate slot 77, for which the pintel 34 (i.e., the pivot axis a) is the cylindrical axis. As shown, the distal end formation 76 is in two parts, a body part 78 fixed to and forming the distal end of part 11', and a clamp part 79 with two spaced end bolts 80 for clamping part 77 to body part 78 via the Steinmann pin, at the slot position which has been determined to align drill guides at 24, 24' with blind distal end bolt holes 22, 22' of the intramedullary nail.

Figure 8:
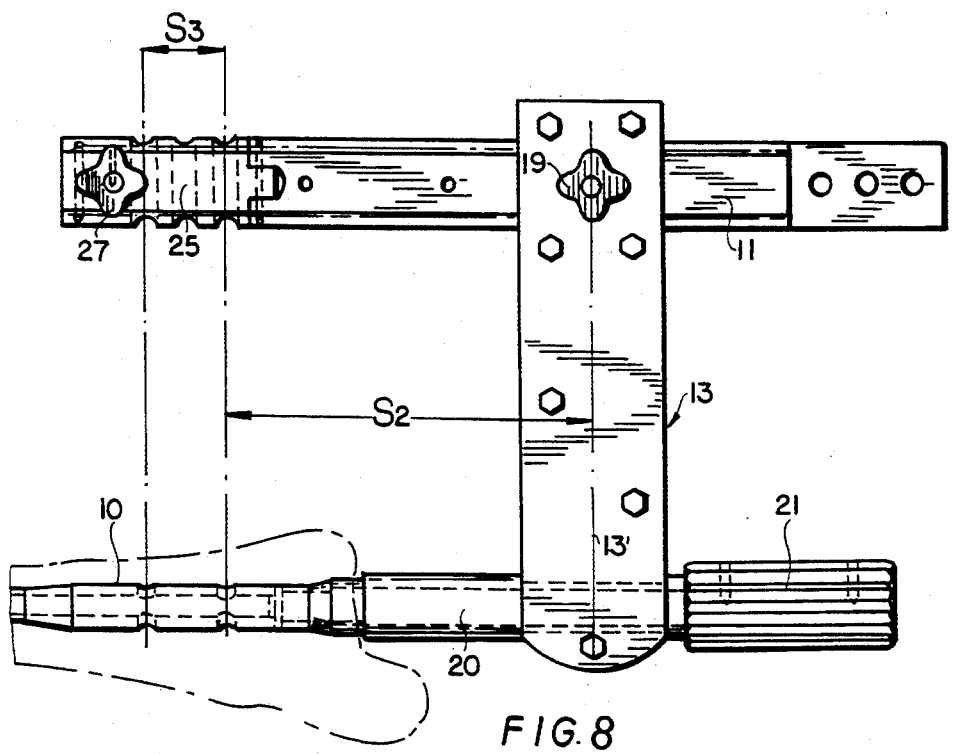
FIG. 8 is a view in side elevation, similar to FIG. 1 but showing a different arrangement of parts.

It has been indicated above that location and drilling of holes for screw insertion via the proximal pair of blind intramedullary-nail holes (23, 23') is not such a problem as to require any use of the metal-detector, or a displacement measurement, or a calculation as described for location of the distal holes 22, 22'. To set the stage for drilling these proximal holes, the described jig will be seen to lend itself to the purpose by detaching proximal part 12 from its clamped relation to arm 13 and by detaching the distally extending template part 11 from the arm 37 of the hinge assembly 35. Noting that part 11 has been provided with a transverse locating bore 18' at offset $S_2$ from the near guide bore 24, FIG. 8 shows that part 11 may be clamped directly to arm 13 in replacement of part 12, with locating-pin 17 alignment with and through the locating bore 18' of part 11. Thus clamped and located, part 11 positions its guide bores 24, 24' in alignment with the proximal bolt holes of nail 10, and proximal screw guides and drill guides may be positioned for drilling upon setting clamp 25. Again, proximal drilling via the drill guides should be without application of force, prior to proximal screw insertion.

Having completed the desired insertion of screws via the bolt holes and into both the distal and proximal fragments of the fractured bone, the jig may be removed, by chuck-release from nail 10, and an external fixator, as of the type described in U.S. Pat. No. Re. 31,809 may be installed, with its respective proximal and distal screw-mounting devices clamped to the now-installed pair of distal screws at one end, and to the now-installed pair of proximal screws at the other end of ball-joint connections to the central body of the fixator.

The described jig structure will be seen to meet all stated objects and to be equally adaptable to a relatively wide range of intramedullary-nail lengths in a given standardized set, wherein the proximal end of each nail in the set has identically the same key formations for correctly oriented engagement by the chucking means associated with mandrel 20 and operating means 21. Each nail in the set should also have its pair of proximal bolt holes (23, 23') at the same standard spacing $S_3$ (e.g. 25 mm), with offset of its bolt hole 23 such as to establish the proximal offset $S_2$ from the central locating axis 13' of arm 13, when chucked. Subject to such points of commonality, the jig of the invention will be seen to be universally applicable for distal-centering as described, for an illustrative set of twelve intramedullary nails, of overall length 280 mm to 500 mm, wherein distal bolt-hole axes 22, 22' are indicated in the following table as distances $D_1$ and $D_2$ from the proximal end of the involved intramedullary nail:

| Nail Size No. | Intramedullary-Nail Set | | |
|---|---|---|---|
| | Length Overall (mm) | $D_1$ (mm) | $D_2$ (mm) |
| 1 | 280 | 240 | 265 |
| 2 | 300 | 260 | 285 |
| 3 | 320 | 280 | 305 |
| 4 | 340 | 300 | 325 |
| 5 | 360 | 320 | 345 |
| 6 | 380 | 340 | 365 |
| 7 | 400 | 360 | 385 |
| 8 | 420 | 380 | 405 |
| 9 | 440 | 400 | 425 |
| 10 | 460 | 420 | 445 |
| 11 | 480 | 440 | 465 |
| 12 | 500 | 460 | 485 |

What is claimed is:

1. An external jig for establishing the axis of a transverse bolt hole in an intramedullary nail that has been implanted in the medullar cavity of both halves of a fractured elongate limb, said jig comprising:
    (a) template structure comprising an elongate distally extending first part having articulating single-axis pivotal connection to an elongate proximally extending second part;
    (b) an offsetting support arm so connected at one end to said proximally extending second part as to establish an offsetting direction which is (i) normal to the direction of second-part elongation, (ii) parallel to said axis of pivotal connection, and (iii) normal to a geometrical first plane which is swept upon articulated displacement of said first part about said axis of pivotal connection;
    (c) chucking means at the other end of said support arm for detachable rigid connection of the support arm to the proximal end of the intramedullary nail, with the offset direction of the arm in a geometric second plane defined by the nail axis and by the axis of the bolt hole and by the elongate direction of said second template part;
    (d) said first template part having a guide bore (i) that is parallel to the offset direction of said arm, and (ii) that when aligned with said second template part, is longitudinally spaced from said arm to the same extent as the bolt-hole axis is spaced from the arm when chucked thereto; and
    (e) means including a metal-detector device adapted for mounting to the distally extending end of said first part and having a central axis of magnetic field symmetry that, thus-mounted, is parallel to the axis of said transverse bore.

2. The external jig of claim 1, wherein said proximally extending second part includes a plurality of longitudinally spaced mounting holes extending normal to the geometric second plane, and wherein the connection of said one end of the support arm to said second part includes a bolt hole which is optionally alignable with a selected one of said mounting holes, and bolt means for securing said arm connection to a selected longitudinal position along said second part via said bolt hole and a selected one of said mounting holes.

3. The external jig of claim 1, wherein said single-axis articulating connection comprises a pivot pintel and a hinging adapter member, journaled in said second part, said first part having a proximal end that is detachably securable to said hinging adapter member.

4. The external jig of claim 1, wherein both of the elongate first and second parts of the template structure have the same cross-section, said cross-section being characterized by a greater moment of inertia in a height dimension taken in the geometric second plane than in a width dimension taken in the geometric first plane.

5. The external jig of claim 1, wherein both of the elongate first and second parts of the template structure have the same cross-section and wherein said first and second parts are detachably connected, the said one end of said offsetting arm being selectively detachably connectable to said proximally extending second part and also detachably connectable to said distally extending one part.

6. The external jig of claim 1, wherein the transverse bolt hole is one of at least two in the intramedullary nail, one of said bolt holes being near the proximal end of the nail, said one end of the support arm having means on a transverse axis of bolting alignment with at least one transverse locating bore along each of said distally extending and proximally extending parts; the longitudinal distance ($S_2$) between the proximal bolt hole in the nail, when chucked, and the transverse axis of bolting alignment of said support arm being equal to the longitudinal distance ($S_2$) between the transverse locating bore of the distally extending part and said guide bore.

7. The external jig of claim 1, in which the distal end of the distally extending first part of the template structure has at least one guide bore that is parallel to said axis of pivotal connection, and means for clamping a K-wire or the like in a selected position in said guide bore, for anchoring reference of the distal end of the distally extending first part to the metaphysis of the bone of the limb after having determined a nail-centered articulated relation of said distally extending first part to said proximally extending second part.

8. The external jig of claim 1, in which the distal end of the distally extending first part of the template structure has a cylindrically arcuate guide slot for a vertically installed Steinmann pin or the like in the metaphysis of the bone beyond the distal end of the intramedullary nail, said guide slot being cylindrical about the articulating single-axis pivotal connection, and selectively operable clamping means for fixing the Steinmann pin in its position in said slot after determination of a nail-centered articulated relation of said distally extending part to said proximally extending part.

9. An external jig for establishing the axis of a transverse bolt hole near the distal end of an intramedullary nail that has been implanted in the medullar cavity of both halves of a fractured elongate limb, with the proximal end of the nail accessible for detachable jig connection thereto, said jig comprising:

(a) a vertically extending offsetting arm having an upper template-supporting end and a lower nail-engageable end, and having means at its lower end for selectively chucked locking engagement to the proximal end of the nail, with the bolt-hole axis and the chucking axis of nail engagement and said offsetting arm all in essentially the same vertical plane;

(b) a template assembly comprising a proximally extending part having a plane of symmetry coincident with said vertical plane, said assembly further including a distally extending part having hinged connection to said proximally extending part on a hinge axis that is parallel to the bolt-hole axis, whereby hinged articulation of said distally extending part is in a horizontal plane that is perpendicular to said vertical plane;

(c) said distally extending member having a guide bore near the distal end thereof and on a guide-bore axis that is normal to said horizontal plane and that is at the same distance from said arm as the distance of the bolt hole from said arm;

(d) a metal-detector with an elongate probe stem mounted to said distally extending part at relatively short longitudinal offset from the guide bore, said stem having a central axis normal to said horizontal plane and parallel to the guide-bore axis, said metal-detector including means establishing a uniformly distributed magnetic field centered on the axis of said stem, and said metal-detector including excitation and detection circuitry producing an electrical-signal output of varying amplitude which peaks at hinge-articulated traverse through proximity to the nail;

(e) displacement-measuring means including a potentiometer mounted to said proximally-extending part and coacting with said distally extending part for generating an electrical signal in response to the instantaneously sensed pivotally displaced position of said distally extending part; and (f) electronic signal-processing means connected to said metal-detector and to said potentiometer (i) for developing and displaying a position value for the "center" position of maximum metal-detector response to nail proximity, and (ii) for developing and separately displaying instantaneous probe-stem position in the same units as the units of the display of the "center" position value.

10. The jig of claim 9, wherein each of said displays is a numerical display.

11. The external jig of claim 9, in which the bolt hole in the nail is one of two like bolt holes on parallel axes that are at a standardized spacing ($S_3$), in which the guide bore of the distally extending member is one of two guide bores on parallel axes that are also at said standardized spacing for axial registration with the respective bolt-hole axes of the nail.

12. The external jig of claim 11, in which the short longitudinal offset at which the probe is mounted to the distally extending part is midway between said guide-bore axes.

13. The method of locating a template guide bore in registry with a blind transverse bolt hole in an intramedullary nail that has been implanted in the medullar cavity of a fractured bone, which comprises the steps of:

(a) mounting the template external to the bone and parallel to the intramedullary nail with the proximal end of the template connected to the proximal end of the nail, the axes of the template guide bore and of the transverse bolt hole being parallel and equidistant from said connection and the distal end of the template being movable in a plane perpendicular to said axes;

(b) selecting a metal-detector having a directional axis of force-field and producing an electrical signal in accordance with detector response to varying proximity of said directional axis to said nail;

(c) mounting said metal-detector to the template to position the directional axis perpendicular to said plane and in non-invasive proximity to the bone;

(d) moving said distal end in said plane and in a direction which traverses registry with the intramedullary nail, whereby to scan the force field from one to the other side of registry with the nail, whereby to produce an electrical output signal having its peak at alignment of the metal-detector axis with the axis of said nail, and which drops symmetrically on opposite sides of scanning through the peak;

(e) measuring and continuously displaying instantaneous position of the metal-detector axis in the course of its scanning motion;

(f) establishing an off-peak reduced threshold level of metal-detector output signal;

(g) calculating, from output-signal traversal of said threshold level on both sides of said peak and from sensed scan position at output-signal traversal of said threshold, a position value for the midpoint between threshold traversals on both sides of the peak, and displaying a calculated positional value identifying said midpoint; and (h) moving said distal end until the display of instantaneous position matches the display of the calculated position.

14. The method of claim 13, in which said first and second displays are numeric.

15. The method of claim 13, and the further step of establishing a stabilizing reference of said distal end to the metaphysis of the bone after establishing the matched displays of step (h).

16. The method of claim 15, in which the stabilizing reference is via a K-wire connection.

17. The method of claim 15, in which the stabilizing reference is via a Steinmann pin that is inserted in the bone prior to performance of steps (d) through (h), and clamping the Steinmann pin to the distal end of the template after establishing the matched displays of step (h).

18. The method of locating a template guide bore in registry with a blind transverse bolt hole in an intramedullary nail that has been implanted in the medullar cavity of a fractured bone, with the proximal end of the nail accessible for detachable jig connection thereto, said method comprising the steps of:

(a) selecting an elongate template member with a guide bore near the distal end of the template and establishing a pivotable connection of the proximal end of the template member to the proximal end of the nail, wherein the connection satisfies the following requirements:

(i) the pivot axis of the connection and the axis of the guide bore of the template member are parallel to the axis of the transverse bolt hole of the nail;

(ii) the axis of the bolt hole and the central axis of the nail and the pivot axis are all contained in a first vertical plane;

(iii) the axis of the guide bore and the pivot axis are in a second vertical plane which has hinged articulation about the pivot axis;

(iv) the template member is at lateral offset from the connection to said nail and is articulatable about the pivot axis in a horizontal plane that is parallel to the central axis of the nail, with the axis of the guide bore and the axis of the bolt hole at the same horizontal offset from the pivot axis, whereby an articulating sweep of the template member over the nail and in the horizontal plane can proceed through a "centered" pivot position wherein the bolt hole and the guide bore are in axial alignment;

(b) digitally tracking increments of articulated displacement of the template member throughout a sweep range in which the axis of the guide bore is swept into and out of axial alignment with the axis of the bolt hole;

(c) selecting and mounting a metal-detector to said template member, wherein the metal-detector establishes a magnetic field having symmetry about a distally located axis in said second vertical plane and parallel to the axis of the guide bore, wherein the magnetic field is sufficiently great as to be affected by nail presence throughout said sweep range, and wherein the metal-detector develops an electrical signal which rises to and falls from a peak amplitude in the course of articulation within said sweep range, the peak amplitude reflecting intersection of the magnetic-field axis with the nail axis;

(d) establishing a threshold level of metal-detector signal at less than said peak level, and coordinating digital tracking increments with threshold traverses of the metal-detector signal;

(e) using the tracked digital increments at both said threshold traverses to compute and display a calculated value of the digital increment value of the articulated location of occurrence of the peak signal amplitude as well as a display of the digital-increment value of the instantaneous articulated displacement position; and (f) adjusting the articulated position of the template member until the display of instantaneous position matches the display of the calculated location.

19. The method of claim 18, in which articulaton is held to the adjusted position of step (f), and including the further steps of (g) using the guide bore as a guide for drilling the bone with drill passage through the bolt hole of the nail, and (h) installing a bone screw in the drilled portion of the bone with bone-screw passage through the bolt hole.

20. An external jig for establishing the axis of a transverse bolt hole in an intramedullary nail that has been implanted in the medular cavity of both halves of a fractured elongate limb, said jig comprising:

(a) an elongate template extending between proximal and distal ends and connected at its proximal end to one end of an offsetting support arm;

(b) chucking means at the other end of the support arm for detachable rigid connection of the support arm to the proximal end of the intramedullary nail, with said template substantially parallel to said nail and with the offset direction of the arm in a geometric plane defined by the nail axis and by the axis of the bolt hole;

(c) said template having a transverse bore on an axis that is parallel to the offset direction of the arm and longitudinally spaced from the arm to the same extent as the bolt-hole axis is spaced from the arm when chucked thereto;

(d) adjustable means carried at the distal end of the template for enabling a fixed reference of the distal end of the template to a portion of the fractured bone which is distal to the distal end of the template, said adjustable means including guide means establishing a guided path of distal-end template displacement transverse to the longituidnal axis of the template and in a plane that is normal to the axis of the transverse bore of the template; and (e) means associated with said adjustable means for releasably clamping an adjusted position along said guide path.

21. The external jig of claim 20, further including a metal-detector which is removably mountable to said template, said metal-detector having a magnetic-field response which has a directional axis and which, when mounted to the template, orients the directional-response axis normal to said plane and in non-invasive proximity to the fractured limb.

* * * * *